(12) United States Patent
Cunningham et al.

(10) Patent No.: US 8,439,912 B2
(45) Date of Patent: May 14, 2013

(54) DE-TENSIONING MECHANISM FOR ARTICULATION DRIVE CABLES

(75) Inventors: James S. Cunningham, Boulder, CO (US); Eric Jones, Livermore, CA (US)

(73) Assignee: Covidien LP, Mansfield, MA (US)

( * ) Notice: Subject to any disclaimer, the term of this patent is extended or adjusted under 35 U.S.C. 154(b) by 716 days.

(21) Appl. No.: 12/714,127

(22) Filed: Feb. 26, 2010

(65) Prior Publication Data
US 2011/0213361 A1 Sep. 1, 2011

(51) Int. Cl.
*A61B 18/14* (2006.01)

(52) U.S. Cl.
USPC .............................................. 606/51; 606/52

(58) Field of Classification Search .................... 606/27, 606/34, 41, 51, 52
See application file for complete search history.

(56) References Cited

U.S. PATENT DOCUMENTS

| | | |
|---|---|---|
| 3,892,228 A | 7/1975 | Mitsui |
| 4,294,233 A | 10/1981 | Takahashi |
| 4,688,555 A | 8/1987 | Wardle |
| 4,941,454 A | 7/1990 | Wood et al. |
| 4,950,273 A | 8/1990 | Briggs |
| 5,167,221 A | 12/1992 | Chikama |
| 5,944,690 A | 8/1999 | Falwell et al. |
| 6,464,629 B1 | 10/2002 | Boone et al. |
| 6,663,588 B2 | 12/2003 | DuBois et al. |
| 7,134,993 B2 | 11/2006 | Lia et al. |
| 7,320,700 B2 | 1/2008 | Cooper et al. |
| 2006/0074383 A1 | 4/2006 | Boulais |

*Primary Examiner* — Michael Peffley
*Assistant Examiner* — Daniel Fowler

(57) ABSTRACT

A surgical instrument includes a housing having an elongated shaft extending distally therefrom. An end effector for treating tissue is supported by the elongated shaft. One or more tensile members extend at least partially through the elongated shaft. A proximal end of a tensile member is operatively coupled to at least one actuator and a distal end is operatively coupled to the end effector such that manipulation of the actuator induces movement of the tensile member to move the end effector. A de-tensioning mechanism is operatively associated with the tensile member to move the tensile member between a first relaxed configuration and a second stressed configuration. The de-tensioning mechanism includes a spacer insertable into a cavity defined in the housing to move the tensile member to the first relaxed configuration and removable from the cavity to move the at least one tensile member to the second stressed configuration.

14 Claims, 5 Drawing Sheets

DE-TENSIONING MECHANISM FOR ARTICULATION DRIVE CABLES

BACKGROUND

1. Technical Field

The present disclosure relates to an apparatus for surgically treating tissue. In particular, the disclosure relates to a mechanism for maintaining a drive cable in a relaxed configuration and imparting a tensile force to the drive cable prior to use of the apparatus.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

Some endoscopic forceps are provided with a distal articulating portion to permit orientation of the jaws relative to a surgical site within the body of a patient. Mechanisms for articulating the distal end of an endoscopic instrument typically include a pair of drive cables or tensile members with distal ends anchored to the articulating portion on opposite sides of an instrument axis. The proximal ends of the drive cables are operatively coupled to an actuator that is responsive to an operator to draw one of the drive cables proximally while simultaneously permitting distal motion in the other drive cable. This motion in the drive cables induces pivotal motion of the distal end of the instrument.

The responsiveness of an articulating mechanism tends to be enhanced when the drive cables are configured to bear a tensile force. An adequate tensile force in the drive cables provides rigidity at the distal end of the instrument that permits a surgeon to perform procedures such as retraction and tissue tensioning. A drive cable under a tensile stress for a prolonged period is subject to creep deformation. Over extended periods of time, five years during storage of the instrument for example, a reduction of the tension in the drive cables may occur due to creep deformation. Accordingly, it may be beneficial to provide an apparatus to permit a surgical instrument to be stored with drive cables in an unstressed state, and to permit an operator to impart a tensile force to the drive cables prior to using the instrument.

SUMMARY

The present disclosure describes a surgical instrument including a housing. The housing supports an actuator that is adapted for manipulation by a user to control the instrument. An elongated shaft extends distally from the housing, and is longitudinally movable with respect to the housing. An end effector adapted for surgically treating tissue is supported by a distal portion of the elongated shaft. A tensile member extends through the elongated shaft, and includes a proximal end operatively coupled to the actuator and a distal end operatively coupled to the end effector such that manipulation of the actuator induces movement of the tensile member to move the end effector. A flange protrudes radially from a proximal portion of the elongated shaft that extends into the housing. A spring is supported within a cavity in the housing such that the spring imparts a distally directed longitudinal force on the flange to bias the elongated shaft in a distal direction. A spacer is insertable into the cavity to maintain the flange and the elongated shaft in a proximal position, and the spacer is removable from the cavity to permit the flange and the elongated shaft to move in a distal direction under the influence of the spring. Movement of the elongated shaft in the distal direction moves the tensile member from a first relaxed configuration to a second stressed configuration.

A distal portion of the elongated shaft may include one or more joints therein to permit the distal portion of the elongated shaft to articulate with respect to the proximal portion of the elongated shaft. The tensile member may be one of pair of articulation cables operatively coupled to the end effector such that relative longitudinal movement between the articulation cables induces articulation of the end effector According to another aspect of the disclosure, a surgical instrument includes a housing and an elongated shaft extending distally from the housing. An end effector for treating tissue is supported by the elongated shaft, and at least one actuator is provided for manipulation by a user to control the end effector. One or more tensile members extend at least partially through the elongated shaft and include a proximal end operatively coupled to the at least one actuator and a distal end operatively coupled to the end effector in such a manner that manipulation of the at least one actuator induces movement of at least one of the tensile members to move the end effector. A de-tensioning mechanism is operatively associated with the tensile members to move one or more of the tensile members between a first relaxed configuration and a second stressed configuration wherein the proximal and distal ends of the tensile member are spaced at a greater distance from one another relative to the first relaxed configuration. The de-tensioning mechanism includes a spacer insertable into a cavity defined in the housing to move the tensile member to the first relaxed configuration and removable from the cavity to move the at least one tensile member to the second stressed configuration.

The elongated shaft may include a proximal portion extending distally from the housing and a distal articulating portion extending distally from the proximal portion. The distal articulating portion may include a joint therein to permit the distal articulating portion to pivot with respect to the proximal portion of the elongated shaft. The tensile members may include a pair of articulation cables operatively coupled to the end effector such that relative longitudinal movement between the articulation cables induces articulation of the end effector.

The de-tensioning mechanism may include a spring arranged to exert a force on the spacer when the spacer is inserted in the cavity and wherein the spring exerts a force on the elongated shaft to move the tensile member to the second stressed configuration when the spacer is removed from the cavity. The spring may be arranged to move the distal end of the at least one tensile member in a distal direction when the spacer is removed from the cavity. The spring may exert a force on an elongate tine of the spacer when the spacer is inserted into the cavity, and the elongate tine may include a sloped surface thereon to facilitate removal of the spacer from the cavity.

The end effector may include a pair of jaw members, and the tensile member may be adapted to move one or more of the one jaw members between an open position substantially spaced from the other of the pair of jaw members and a closed position wherein the jaw members are closer together. One or both of the jaw members may be coupled to a source of electrical energy.

According to another aspect of the disclosure, a surgical instrument includes a housing and an elongated shaft extending distally from the housing. An end effector for treating tissue is supported by the elongated shaft, and at least one actuator is provided for manipulation by a user to control the end effector. One or more tensile members extend at least partially through the elongated shaft and include a proximal end operatively coupled to the at least one actuator and a distal end operatively coupled to the end effector in such a manner that manipulation of the at least one actuator induces movement of at least one of the tensile members to move the end effector. A de-tensioning mechanism is operatively associated with the tensile members to move one or more of the tensile members between a first relaxed configuration and a second stressed configuration. The de-tensioning mechanism is operable to move the distal end of the tensile member between a position a first distance from the housing and a second position wherein the distal end of the tensile member is a second distance from the housing. The second distance is greater than the first such that the tensile member is in the stressed configuration when the distal end of the tensile member is at the second position.

The de-tensioning mechanism may be operable to move the end effector in a distal direction relative to the housing to move the tensile member to the second stressed configuration. The de-tensioning mechanism may include a spacer insertable into a cavity defined in the housing to move the end effector in a proximal direction and removable from the cavity to move the end effector in the distal direction.

According to another aspect of the disclosure, a surgical instrument includes a surgical instrument includes a housing and an elongated shaft extending distally from the housing. An end effector for treating tissue is supported by the elongated shaft, and at least one actuator is provided for manipulation by a user to control the end effector. One or more tensile members extend at least partially through the elongated shaft and include a proximal end operatively coupled to the at least one actuator and a distal end operatively coupled to the end effector in such a manner that manipulation of the at least one actuator induces movement of at least one of the tensile members to move the end effector. A de-tensioning mechanism is operatively associated with the tensile members to move one or more of the tensile members between a first relaxed configuration and a second stressed configuration. The de-tensioning mechanism is operable to move the end effector between a position a first distance from the housing and a second position wherein the end effector is second distance from the housing. The second distance is greater than the first such that the tensile member is in the stressed configuration when the distal end of the tensile member is at the second position.

The de-tensioning mechanism may include a spacer insertable into a cavity defined in the housing to move the end effector to the first distance from the housing and removable from the cavity to move the end effector to the second distance from the housing.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
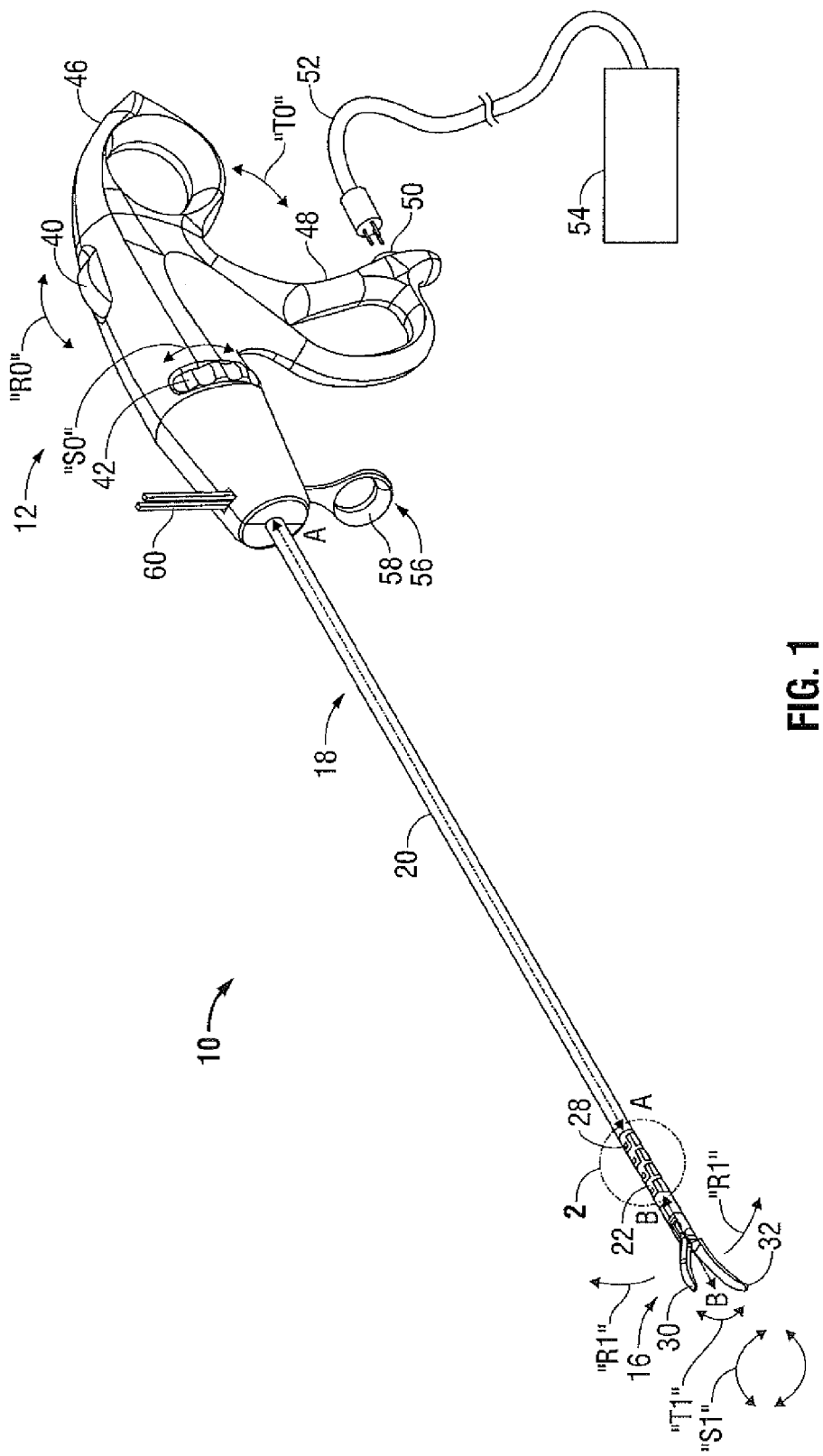
FIG. 1 is a perspective view of a surgical instrument in accordance with an embodiment of the present disclosure.

Referring initially to FIG. 1, an embodiment of an electrosurgical instrument is depicted generally as 10. The instrument 10 includes a housing 12 for remotely supporting an end effector 16 through an elongated shaft 18. Although this configuration is typically associated with instruments for use in endoscopic surgical procedures, various aspects of the present disclosure may be practiced in connection with traditional open procedures as well.

Elongated shaft 18 includes a proximal portion 20 extending from the housing 12 and an articulating distal portion 22 supporting the end effector 16. The proximal portion 20 defines a longitudinal axis A-A, and is sufficiently long to position the end effector 16 through a cannula (not shown). The articulating distal portion 22 defines at least one joint 28 between the proximal portion 20 of the elongated shaft 18 and the end effector 16 permitting the end effector 16 to articulate or pivot relative to the longitudinal axis A-A. The end effector 16 defines an end effector axis B-B, which may be aligned with the longitudinal axis A-A to facilitate insertion of the end effector 16 through the cannula, and thereafter moved to orient the end effector 16 relative to a surgical site within the body of a patient.

The end effector 16 includes a pair of opposing jaw members 30 and 32. The jaw members 30, 32 are operable from the housing 12 to move between an open configuration to receive tissue, and a closed configuration to clamp the tissue and impart an appropriate clamping force thereto. When the end effector 16 is in the open configuration, a distal portion of each of the jaw members 30, 32 is spaced from the distal portion of the other of the jaw members 30, 32. When the end effector 16 is in the closed configuration, the distal portions of the jaw members 30, 32 are closer together. The end effector 16 is configured for bilateral movement wherein both jaw members 30 and 32 move relative to the end effector axis B-B as the end effector 16 is moved between the open and closed configurations. However, unilateral motion is also contemplated wherein one of the jaw members 30, 32, e.g., 32 remains stationary relative to the end effector axis B-B and the other of the jaw members 30, 32, e.g., 30 is moveable relative to the end effector axis B-B.

The housing 12 supports various actuators that are responsive to manipulation by an operator to induce these and other movements of the end effector 16. These actuators include an articulation wheel 40, which is operable to articulate the distal portion 22 of the elongated shaft 18 with respect to the longitudinal axis A-A. As described in greater detail below, the articulation wheel 40 is operatively coupled to the articulating distal portion 22 of the elongated shaft 18 by a pair of tensile members, such as drive cables 66, 68 (see FIGS. 3 and 5), such that rotation of the articulation wheel 40 in the direction of arrows "R0" induces pivotal motion of the end effector 16 in the direction of arrows "R1" about the joints 28. The responsiveness of the end effector 16 to pivot upon rotation of the articulation wheel 40 is affected, in part, by a tensile force carried in the drive cables 66, 68 as described in greater detail below.

Other actuators supported by the housing 12 may include a roll knob 42 and a movable handle 46. The roll knob 42 is operable to rotate the end effector 16 about the end effector axis B-B. Rotation of the roll knob 42 in the direction of arrow "S0" induces rotational motion of the end effector 16 in the direction of arrows "S1." The articulation wheel 40 and roll knob 42 cooperate to permit the end effector 16 to be appropriately positioned and oriented to effectively engage tissue. Once the end effector 16 is positioned and oriented, the surgeon may approximate the movable handle 46 relative to a stationary handle 48 to move the jaw members 30, 32 to the closed configuration. Separation of the movable handle 46 from the stationary handle 48 moves the jaw members 30, 32 to the open configuration. Thus, motion of the movable handle 46 in the direction of arrows "T0" induces motion in the end effector 16 in the direction of arrows "T1."

The stationary handle 48 is provided with a power port 50 for receiving an electrosurgical cable 52. The cable 52 is in electrical communication with a source of electrosurgical energy such as electrosurgical generator 54. The electrosurgical generator 54 serves to produce electrosurgical energy and also to control and monitor the delivery of the electrosurgical energy to the instrument 10. Various types of electrosurgical generators 54, such as those generators provided by Covidien—Energy-based Devices, of Boulder, Colo., may be suitable for this purpose. Electrosurgical generator 54 may include a foot pedal (not shown), or other actuator to initiate and terminate the delivery of electrosurgical energy to the instrument 10. The power port 50 on the stationary handle 48 is in electrical communication with at least one of the jaw members 30, 32 such that the electrosurgical energy supplied by the generator 54 may be delivered to tissue clamped in the end effector 16.

Instrument 10 is provided with a removable spacer 56. The spacer 56 includes a finger loop 58 at a lower end thereof and an elongate pair of tines 60 at an upper end. The spacer 56 may be grasped by the finger loop 58 and drawn out of the instrument 10. As described below with reference to FIGS. 4A and 4B, when the spacer 56 is installed, the instrument 10 may be stored over a long term with the drive cables 66, 68 in a relaxed configuration. The spacer 56 may be removed prior to use of the instrument 10 to impart a tensile force to the drive cables 66, 68 as described below with reference to FIG. 4B.

Figure 2:
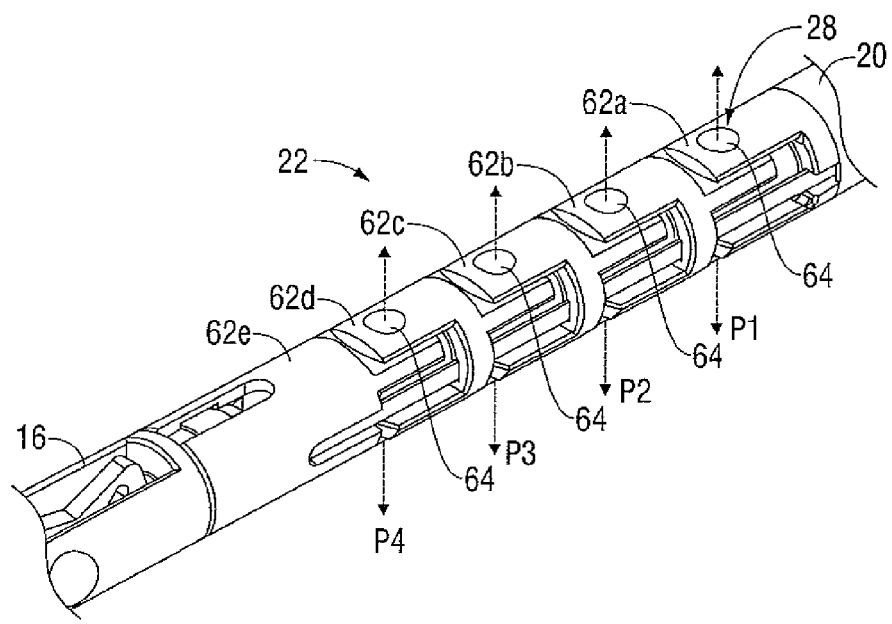
FIG. 2 is an enlarged perspective view of the area of detail identified in FIG. 1 depicting a distal articulating portion of the instrument.

Referring now to FIG. 2, the articulating distal portion 22 of the elongated shaft 18 includes a plurality of discrete links 62a, 62b, 62c, 62d and 62e. A proximal-most link 62a is fixedly coupled to the proximal portion 20 of the elongated shaft 18, and a distal-most link 62e supports the end effector 16. A plurality of intermediate links 62b, 62c, and 62d extend between the proximal-most link 62a and the distal-most link 62e. Each of the links 62a, 62b, 62c, 62d and 62e is pivotally coupled to at least one neighboring link 62a, 62b, 62c, 62d 62e by a pivot pin 64. The pivot pins 64 define four pivot axes P1, P2, P3 and P4 about which the neighboring links 62a, 62b, 62c, 62d and 62e may pivot to define the joints 28. In the embodiment depicted in FIG. 2, each of the pivot pins 64 are arranged in a substantially parallel manner such that the distal end 22 of the elongated shaft 18 is permitted to pivot in a single plane to orient the end effector 16. In other embodiments, pivot axes (not shown) may be oriented orthogonally or obliquely with respect to one another to permit the distal end to pivot in multiple planes. In still other embodiments, the joints 28 may be defined with a flexible or bendable portion (not shown) of the elongated shaft 18.

Figure 3:
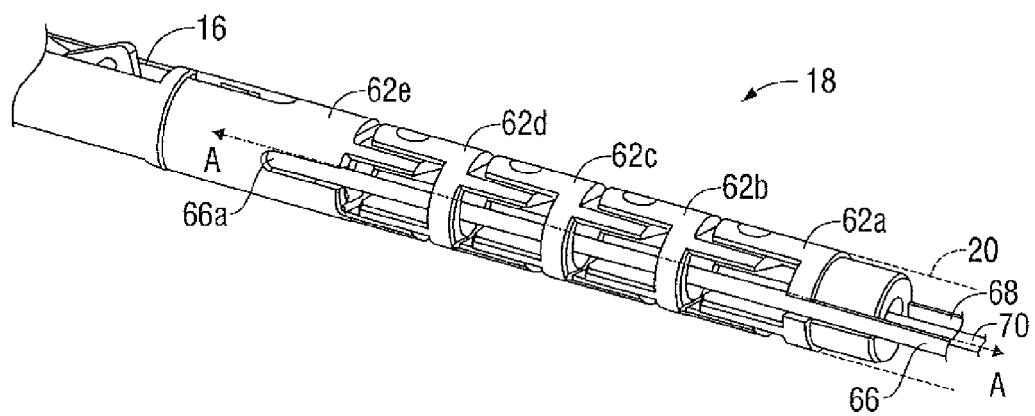
FIG. 3 is another perspective view of the distal articulating portion of the instrument.

In order pivot the links 62a, 62b, 62c, 62d, 62e about the respective axes P1, P2, P3, P4, a pair of longitudinally extending and reciprocating drive cables 66 and 68 are provided as depicted in FIG. 3. A distal end 66a of the drive cable 66 is affixed to the distal-most link 62e on an opposite lateral side of the distal-most link 62e with respect to a distal end 68a (FIG. 6A) of drive cable 68. The drive cables 66, 68 extend from the distal-most link 62e proximally through the links 62d, 62c, 62b, 62a and through the proximal portion 20 of the elongated shaft 18 into the housing 12 (FIG. 1). In the housing 12, the articulation drive cables 66 and 68 are operatively associated with articulation wheel 40 as described below with reference to FIG. 5. Distal advancement of one of the drive cables 66 or 68 and simultaneous proximal retraction of the other of drive cables 66 or 68 function to cause links 62a, 62b, 62c, 62d and 62e to pivot relative to each other, thereby causing a bend in articulating distal portion 22.

An additional tensile member, such as drive cable 70, may extend through the elongated shaft 18. A distal end of the drive cable 70 may be operatively coupled to the end effector 16 to move the jaw members 30, 32 (FIG. 1) between the open and closed configurations. Longitudinal motion of the drive cable 70 may be translated into pivotal motion of the jaw members 30, 32 as described, for example, in U.S. Pat. No. 7,083,618 to Couture et al. A proximal end of the drive cable 70 may be operatively coupled to movable handle 46 (FIG. 1) such that longitudinal motion of the drive cable 70 may be induced by manipulation of the movable handle 46.

Figure 4A:
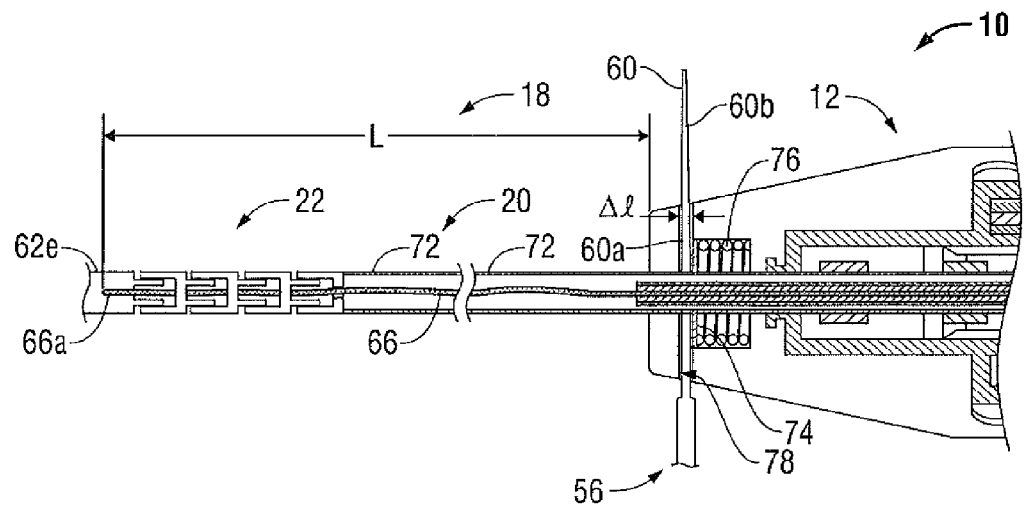
FIG. 4A is a partial, cross-sectional side view of the instrument in a first configuration wherein a spacer is installed.

Referring now to FIG. 4A, the instrument 10 is depicted in a first configuration wherein the removable spacer 56 is installed in the instrument 10 and an articulation drive cable 66 is in a relaxed configuration. The tines 60 of the spacer 56 are laterally separated to permit the spacer 56 to straddle an outer tubular member 72 of the proximal portion 20 of the elongated shaft 18. The tines 60 are engaged by a flange 74 that extends radially from the outer tubular member 72 and is fixedly coupled to the outer tubular member. A spring 76 exerts a force on the flange 74 to bias the flange 74 in a distal direction against the tines 60 and also biasing the tines 60 against a proximal-facing wall 78 of the housing 12. A portion 60a of the tines 60 that is in contact with the flange 74 has a thickness of "Δl," and an upper portion of the tines 60b includes a gradual slope to facilitate removal of the tines from the instrument 10.

When the spacer 56 is installed, the spacer 56 maintains the flange 74 and the elongated shaft 18 in a proximal position wherein the elongated shaft 18 extends from the housing 12 such that the distal end 66a of the drive cable 66 is disposed at a distance "L" from the housing 12. The drive cable 66 exhibits a sufficient length such that the drive cable 66 is in a relaxed or neutral state when the distal end 66a is at the distance "L" from the housing 12.

Figure 4B:
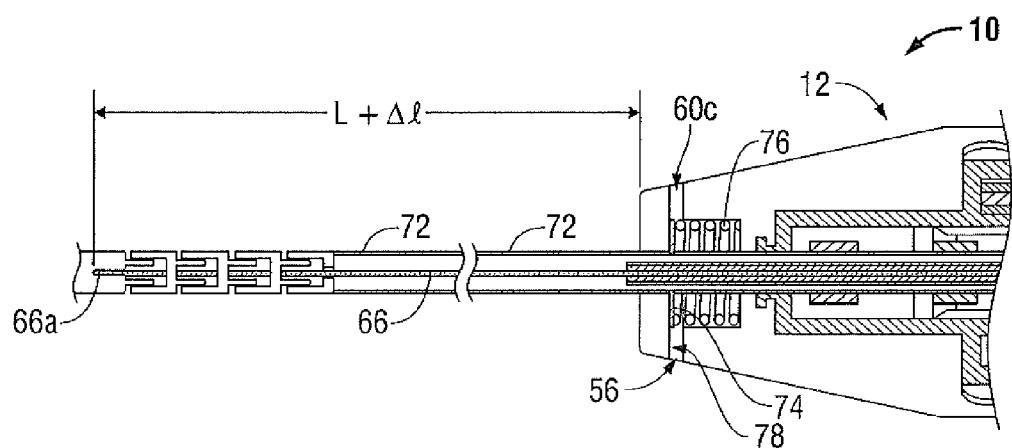
FIG. 4B is a partial, cross sectional side view of the instrument in a second configuration wherein the spacer has been removed.

Referring now to FIG. 4B, the instrument 10 is depicted in a second configuration wherein the spacer 56 has been removed. With the spacer 56 removed, the spring 76 is permitted to extend distally in a longitudinal direction. The flange 74 is driven distally by the spring 76 through a spacer cavity 60c until the drive flange 74 abuts the proximal-facing wall 78 of the housing 12. Since the flange 74 is fixedly coupled to the outer tubular member 72 of the elongated shaft 18, the outer tubular member 72 is also driven distally by the spring 76 to a distal position with respect to the housing 12. The distal-most link 62e and thus the distal end 66a of the drive cable 66 is also driven distally until the distal end 66a of the drive cable 66a is disposed at a distance "L+Δl" from the housing 12. A proximal end 66b (FIG. 5) of the drive cable 66 is coupled to the housing 12 as described below with reference to FIG. 5. The drive cable 66 exhibits length such that the drive cable 66 is in a stretched or tensile state when the distal end 66a is at the distance of "L+Δl" from the housing 12. Thus, removing the spacer 56 from the cavity 60e in the instrument 10 imparts a tensile force to the drive cable 66.

The articulating drive cable 68 and jaw drive cable 70 (FIG. 3) are similarly arranged such that removing the spacer 56 from the instrument 10 also imparts a tensile force to the drive cables 68, 70. With a tensile force imparted to the drive cables 66, 68, a surgeon may actuate an articulation mechanism 80 (FIG. 5) to articulate the end distal portion 22 of the elongated shaft 18. The surgeon may also actuate the movable handle 46 to move the jaw members 30, 32 (FIG. 1) between the open and closed configurations.

Figure 5:
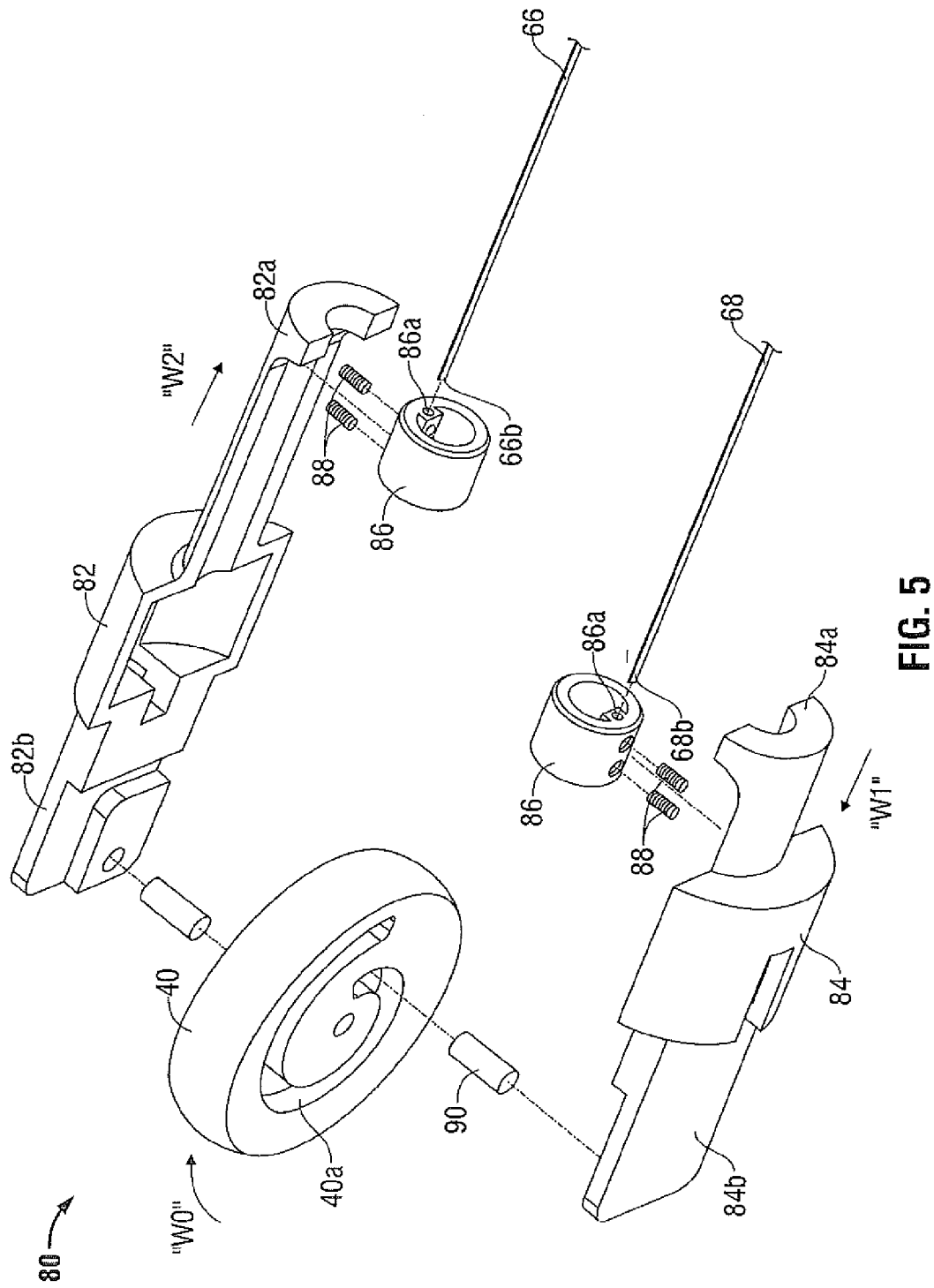
FIG. 5 is an exploded, perspective view of an articulation mechanism of the instrument.
Figure 6A:
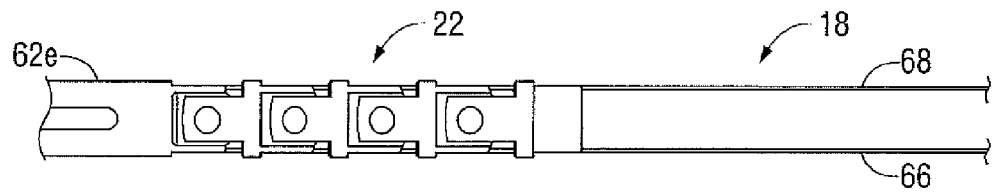
FIG. 6A is a top view of the distal articulating portion of the instrument in a neutral position.

Referring now to FIG. 5, articulation mechanism 80 is depicted independent of the remaining instrument components. The articulation mechanism 80 includes a pair of shuttles 82, and 84 to advance and retract the drive cables 66, 68. Shuttles 82 and 84 are provided with distal hooks 82a and 84a, which engage and alternatively retract a pair of collars 86. Each of the collars 86 includes a bore 86a for receipt of a proximal end 66b, 68b of the drive cables 66, 68. Set screws 88 secure the drive cables 66, 68 within bores 86a.

Figure 6B:
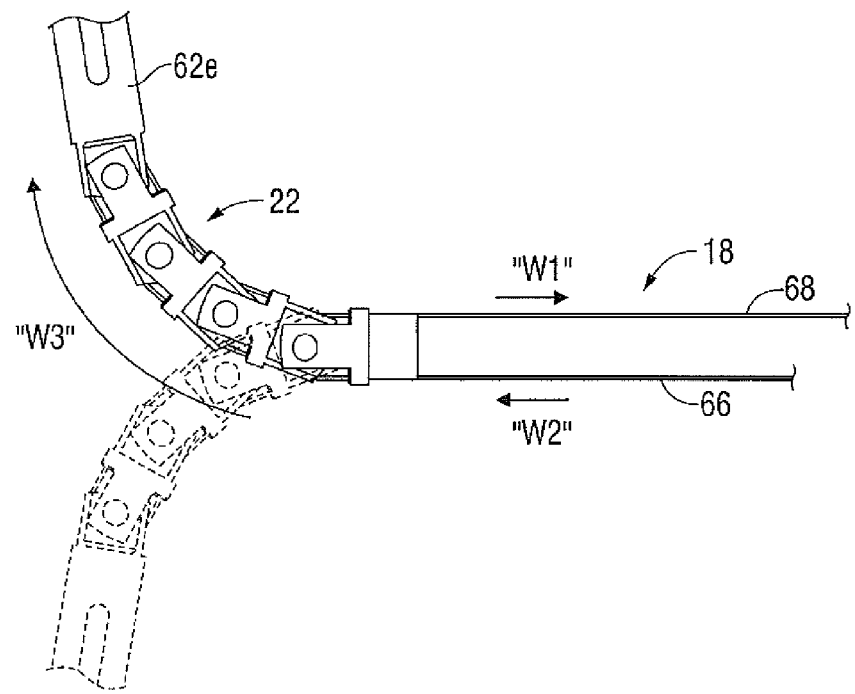
FIG. 6B is a top view of the distal articulating section of the instrument in an articulated position.

Shuttles 82 and 84 have respective proximal ends 82b and 84b that are configured to engage articulation wheel 40 with pins 90 extending therefrom. The pin 90 that extends from the proximal end 84b of shuttle 84 engages a spiral groove 40a inscribed into a lateral side of the articulation wheel 40. On an opposite lateral side of the articulation wheel 40, a second spiral groove (not shown) is inscribed in an opposite orientation and is engaged by the pin 90 extending from the proximal end 82b of the shuttle 82. The spiral grooves, e.g., groove 40a, permit rotational movement of the articulation wheel 40 to be translated into longitudinal and reciprocal motion of shuttles 82 and 84. Rotation of the articulation wheel 40 in the direction of arrow "W0" induces the shuttle 84 and the drive cable 68 to move in the direction of arrow "W1." Longitudinal motion of the drive cable 68 in the direction of arrow "W1" induces the distal portion 22 of the elongated shaft 18 to move from a straight configuration (FIG. 6A) to an articulated configuration in the direction of arrow "W3" (FIG. 6B). Rotation of the articulation wheel 40 in a direction opposite the direction of arrow "W0" induces an opposite motion such that the distal portion 22 of the elongated shaft 18 is articulated in an opposite direction as depicted in phantom in FIG. 6B.

It should be noted that, since the drive cables 66 and 68 are secured to the distal-most link 62e as described above, as one of the drive cables 66 or 68 is pulled proximally by respective hook 82a or 84a, the other of drive cables 66 or 68 is automatically drawn distally. Thus, there is no need for the shuttles 82, 84 to provide a structure for pushing or driving either of the collars 86 distally.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a housing supporting at least one actuator thereon, the actuator adapted for manipulation by a user to control the instrument;
   an elongated shaft extending distally from the housing, the elongated shaft longitudinally movable with respect to the housing;
   an end effector supported by a distal portion of the elongated shaft, the end effector adapted for surgically treating tissue;
   at least one tensile member extending through the elongated shaft, the at least one tensile member including a proximal end operatively coupled to the at least one actuator and a distal end operatively coupled to the end effector such that manipulation of the at least one actuator induces movement of the at least one tensile member to move the end effector;
   a flange protruding radially from a proximal portion of the elongated shaft that extends into the housing;
   a spring within a cavity defined in the housing, the spring supported in the cavity such that the spring imparts a distally directed longitudinal force on the flange to bias the elongated shaft in a distal direction; and
   a spacer insertable into the cavity to maintain the flange and the elongated shaft in a proximal position, the spacer removable from the cavity to permit the flange and the elongated shaft to move in a distal direction under the influence of the spring, wherein movement of the elongated shaft in the distal direction moves the at least one tensile member from a first relaxed configuration to a second stressed configuration.

2. The surgical instrument according to claim 1, wherein the distal portion of the elongated shaft defines at least one joint therein to permit the distal portion of the elongated shaft to articulate with respect to the proximal portion of the elongated shaft.

3. The surgical instrument according to claim 2, wherein the at least one tensile member includes a pair of articulation cables operatively coupled to the end effector such that relative longitudinal movement between the articulation cables induces articulation of the end effector.

4. A surgical instrument, comprising:
   a housing having an elongated shaft extending distally therefrom, the elongated shaft supporting an end effector for treating tissue;
   at least one actuator adapted for manipulation by a user to control the end effector;
   at least one tensile member extending at least partially through the elongated shaft, the at least one tensile member including a proximal end operatively coupled to the at least one actuator and a distal end operatively coupled to the end effector such that manipulation of the at least one actuator induces movement of the at least one tensile member to move the end effector;
   a de-tensioning mechanism operatively associated with the at least one tensile member to move the at least one tensile member between a first relaxed configuration to a second stressed configuration wherein the proximal and distal ends of the at least one tensile member are spaced at a greater distance from one another relative to the first relaxed configuration, the de-tensioning mechanism including a spacer insertable into a cavity defined in the housing to move the tensile member to the first relaxed configuration and removable from the cavity to move the at least one tensile member to the second stressed configuration.

5. The surgical instrument according to claim 4, wherein the elongated shaft includes a proximal portion extending distally from the housing and a distal articulating portion extending distally from the proximal portion, the distal articulating portion defining at least one joint therein to permit the distal articulating portion to pivot with respect to the proximal portion of the elongated shaft.

6. The surgical instrument according to claim 5, wherein the at least one tensile member includes a pair of articulation cables operatively coupled to the end effector such that relative longitudinal movement between the articulation cables induces articulation of the end effector.

7. The surgical instrument according to claim 4, wherein the de-tensioning mechanism includes a spring arranged to exert a force on the spacer when the spacer is inserted in the cavity and wherein the spring exerts a force to move the at least one tensile member to the second stressed configuration when the spacer is removed from the cavity.

8. The surgical instrument according to claim 7, wherein the spring is arranged to move the distal end of the at least one tensile member in a distal direction when the spacer is removed from the cavity.

9. The surgical instrument according to claim 7, wherein the spring exerts a force on an elongate tine defined by the spacer when the spacer is inserted into the cavity, and wherein the elongate tine includes a sloped surface thereon to facilitate removal of the spacer from the cavity.

10. The surgical instrument according to claim 4, wherein the end effector includes a pair of jaw members, and wherein the at least one tensile member is operable to move at least one jaw member between an open position substantially spaced from the other of the pair of jaw members and a closed position wherein the jaw members are closer together.

11. The surgical instrument according to claim 10, wherein at least one of the pair of jaw members is coupled to a source of electrical energy.

12. A surgical instrument, comprising:
a housing having an elongated shaft extending distally therefrom, the elongated shaft supporting an end effector for treating tissue;
at least one actuator adapted for manipulation by a user to control the end effector;
at least one tensile member extending at least partially through the elongated shaft, the at least one tensile member including a proximal end operatively coupled to at least one actuator and a distal end operatively coupled to the end effector such that manipulation of the at least one actuator induces movement of the at least one tensile member to move the end effector; and
a de-tensioning mechanism operatively associated with the at least one tensile member to move the at least one tensile member between a first relaxed configuration wherein the distal end of the at least one tensile member is disposed at a first distance from the housing and a second stressed configuration wherein the distal end of the at least one tensile member is disposed at a second distance from the housing, the second distance greater than the first,
wherein the de-tensioning mechanism includes a spacer insertable into a cavity defined in the housing to move the end effector in a proximal direction and removable from the cavity to move the end effector in the distal direction.

13. The surgical instrument according to claim 12, wherein the de-tensioning mechanism is operable to move the end effector in a distal direction relative to the housing to move the at least one tensile member to the second stressed configuration.

14. A surgical instrument, comprising:
a housing having an elongated shaft extending distally therefrom, the elongated shaft supporting an end effector for treating tissue;
at least one actuator adapted for manipulation by a user to control the end effector;
at least one tensile member extending at least partially through the elongated shaft, the at least one tensile member including a proximal end operatively coupled to the at least one actuator and a distal end operatively coupled to the end effector such that manipulation of the at least one actuator induces movement of the at least one tensile member to move the end effector; and
a de-tensioning mechanism operatively associated with the at least one tensile member to move the at least one tensile member between a first relaxed configuration wherein the end effector is disposed at a first distance from the housing and a second stressed configuration wherein the end effector is disposed at a second distance from the housing, the second distance greater than the first,
wherein the de-tensioning mechanism includes a spacer insertable into a cavity defined in the housing to move the end effector to the first distance from the housing and removable from the cavity to move the end effector to the second distance from the housing.

* * * * *